US012605113B2

(12) United States Patent
    Guilardi et al.

(10) Patent No.: US 12,605,113 B2
(45) Date of Patent: Apr. 21, 2026

(54) TEMPLATE DEVICE FOR REPEATABLE PLACEMENT OF CHEST ELECTRODES FOR ECG

(71) Applicant: AliveCor, Inc., Mountain View, CA (US)

(72) Inventors: Brian Guilardi, San Jose, CA (US); Siva Somayajula, Saratoga, CA (US)

(73) Assignee: Alivecor, Inc., Mountain View, CA (US)

( * ) Notice: Subject to any disclaimer, the term of this patent is extended or adjusted under 35 U.S.C. 154(b) by 281 days.

(21) Appl. No.: 18/422,604

(22) Filed: Jan. 25, 2024

(65) Prior Publication Data

US 2025/0241590 A1    Jul. 31, 2025

(51) Int. Cl.
    *A61B 5/00* (2006.01)

(52) U.S. Cl.
    CPC .......... *A61B 5/6841* (2013.01); *A61B 5/6823* (2013.01); *A61B 2560/04* (2013.01)

(58) Field of Classification Search
    CPC .............................. A61B 5/282; A61B 5/6823
    See application file for complete search history.

(56) References Cited

U.S. PATENT DOCUMENTS

| | | | |
|---|---|---|---|
| 3,525,330 A | 8/1970 | Greene | |
| 4,593,698 A | 6/1986 | Athans | |
| 6,173,198 B1 | 1/2001 | Schulze et al. | |

FOREIGN PATENT DOCUMENTS

| | | |
|---|---|---|
| CN | 101828915 A | 9/2010 |
| EP | 0381480 B1 | 5/1995 |
| WO | 2023212542 A2 | 11/2023 |

OTHER PUBLICATIONS

PCT International Search Report and Written Opinion from related PCT Application No. PCT/US2025/012917, mailed on Mar. 21, 2025 (14 pages).

*Primary Examiner* — Eun Hwa Kim
(74) *Attorney, Agent, or Firm* — Womble Bond Dickinson (US) LLP

(57) ABSTRACT

Disclosed are devices and methods for determining and memorializing chest electrode placement locations on a user. The device utilizes two datum reference points in the patient's anatomy, the Jugular notch and the Xiphoid process, which are easily found and repeatable and which serve to ensure the device is in the correct position to memorialize chest electrode placement locations. The device may comprise a first plate and a second plate operatively coupled to the first plate so that the second plate slides along a vertical axis of the first plate and the first plate slides along a vertical access of the second plate. The device may further comprise a template grid having a plurality of cells printed thereon. The template grid may have a coordinate system for identifying each of the plurality of cells. The template grid may be modified to indicate a set of chest electrode placement locations on the user.

19 Claims, 15 Drawing Sheets

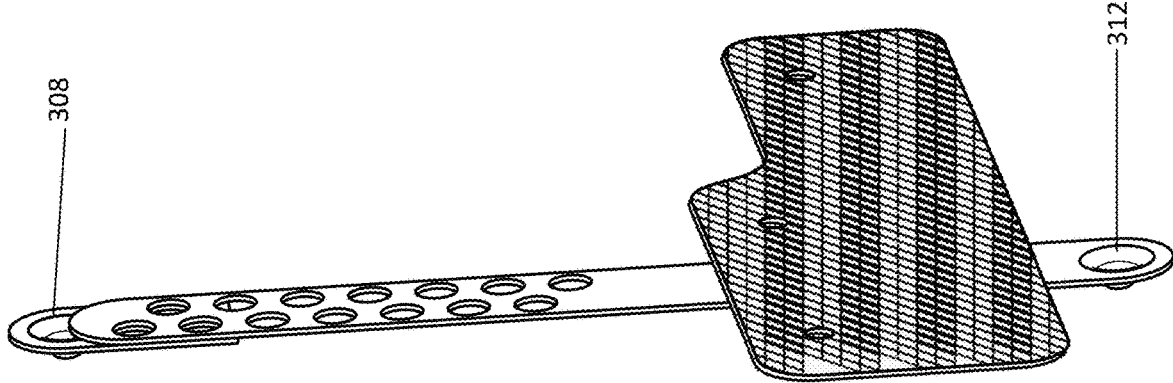
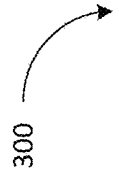
*FIG. 3C*

315

Mid Clavical Line

Anterior Axillary Line

Mid Axillary Line

Angle of Louis

700

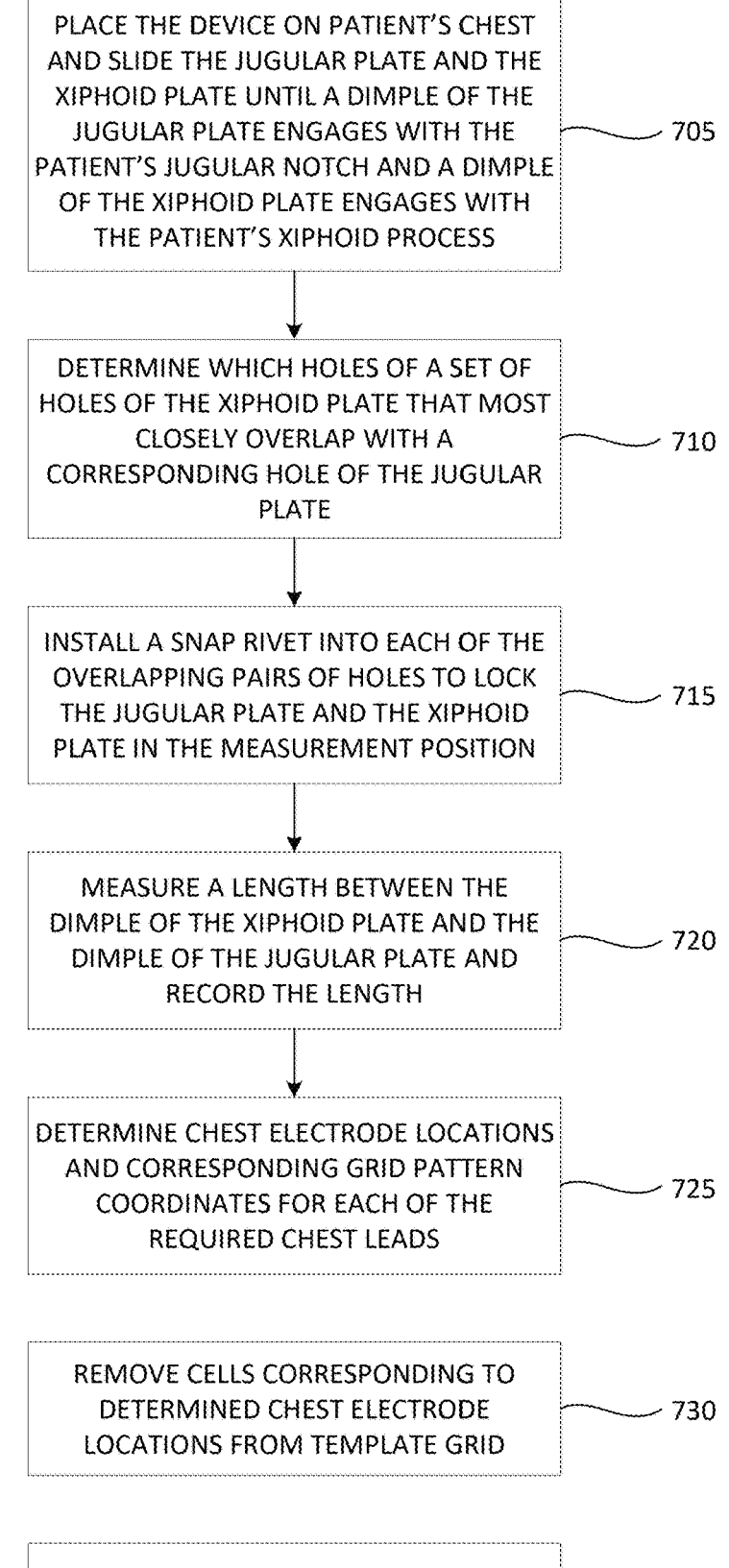

PLACE THE DEVICE ON PATIENT'S CHEST AND SLIDE THE JUGULAR PLATE AND THE XIPHOID PLATE UNTIL A DIMPLE OF THE JUGULAR PLATE ENGAGES WITH THE PATIENT'S JUGULAR NOTCH AND A DIMPLE OF THE XIPHOID PLATE ENGAGES WITH THE PATIENT'S XIPHOID PROCESS — 705

DETERMINE WHICH HOLES OF A SET OF HOLES OF THE XIPHOID PLATE THAT MOST CLOSELY OVERLAP WITH A CORRESPONDING HOLE OF THE JUGULAR PLATE — 710

INSTALL A SNAP RIVET INTO EACH OF THE OVERLAPPING PAIRS OF HOLES TO LOCK THE JUGULAR PLATE AND THE XIPHOID PLATE IN THE MEASUREMENT POSITION — 715

MEASURE A LENGTH BETWEEN THE DIMPLE OF THE XIPHOID PLATE AND THE DIMPLE OF THE JUGULAR PLATE AND RECORD THE LENGTH — 720

DETERMINE CHEST ELECTRODE LOCATIONS AND CORRESPONDING GRID PATTERN COORDINATES FOR EACH OF THE REQUIRED CHEST LEADS — 725

REMOVE CELLS CORRESPONDING TO DETERMINED CHEST ELECTRODE LOCATIONS FROM TEMPLATE GRID — 730

(OPTIONALLY) CUT/TRIM TEMPLATE GRID TO MATCH ANATOMY OF THE PATIENT — 735

*FIG. 7*

TEMPLATE DEVICE FOR REPEATABLE PLACEMENT OF CHEST ELECTRODES FOR ECG

TECHNICAL FIELD

The present disclosure relates to medical devices, systems, and methods and in particular, to devices for determining and memorializing electrode placement locations on a user.

BACKGROUND

Cardiovascular diseases are the leading cause of death in the world. In 2008, 30% of all global deaths can be attributed to cardiovascular diseases. It is also estimated that by 2030, over 23 million people will die from cardiovascular diseases annually. Cardiovascular diseases are prevalent across populations of first and third world countries alike, and affect people regardless of socioeconomic status.

Arrhythmia is a cardiac condition in which the electrical activity of the heart is irregular or is faster (tachycardia) or slower (bradycardia) than normal. Although many arrhythmias are not life-threatening, some can cause cardiac arrest and even sudden cardiac death. Indeed, cardiac arrhythmias are one of the most common causes of death when traveling to a hospital. Atrial fibrillation (A-fib) is the most common cardiac arrhythmia. In A-fib, electrical conduction through the ventricles of the heart is irregular and disorganized. While A-fib may cause no symptoms, it is often associated with palpitations, shortness of breath, fainting, chest pain or congestive heart failure and also increases the risk of stroke. A-fib is usually diagnosed by taking an electrocardiogram (ECG) of a subject. To treat A-fib, a person may take medications to slow heart rate or modify the rhythm of the heart. Persons may also take anticoagulants to prevent stroke or may even undergo surgical intervention including cardiac ablation to treat A-fib. In another example, an ECG may provide decision support for Acute Coronary Syndromes (ACS) by interpreting various rhythm and morphology conditions, including Myocardial Infarction (MI) and Ischemia.

An ECG provides a number of waveforms that represent the electrical activity of a person's heart. An ECG monitoring device may comprise a set of electrodes for recording these waveforms (also referred to herein as "taking an ECG") of the person's heart. A typical heartbeat may include several variations of electrical potential, which may be classified into waves and complexes, including a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. ECG waveforms may be analyzed for various indicators that are useful in detecting cardiac events or status, such as cardiac arrhythmia detection and characterization.

Often, a person with A-fib (or other type of arrhythmia) is monitored for extended periods of time to manage the disease. The American Heart Association and the European Society of Cardiology recommends that a 12-lead ECG should be acquired as early as possible for people with possible ACS when symptoms present. Prehospital ECG has been found to significantly reduce time-to-treatment and shows better survival rates. The time-to-first-ECG is so vital that it is a quality and performance metric monitored by several regulatory bodies. According to the national health statistics for 2015, over 7 million people visited the emergency department (ED) in the United States (U.S.) with the primary complaint of chest pain or related symptoms of ACS. In the US, ED visits are increasing at a rate of or 3.2% annually and outside the U.S. ED visits are increasing at 3% to 7%, annually.

As a result of this, there are a number of ECG measurement devices which can provide ECG monitoring on an ad-hoc basis to continuously monitor the electrical activity of a user's cardiovascular system. These devices range from larger form factor devices such as Holter monitors to smaller form factor devices such as smartwatches and handheld portable ECG monitors etc. that allow for at home monitoring. Many of these devices are capable of synchronizing with a computing device (e.g., laptop, smart phone, etc.) so as to transmit recorded waveforms to the computing device for storage and display.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIGS. 3A-3D illustrates a device for determining and memorializing chest electrode placement locations, in accordance with some embodiments of the present disclosure.

FIG. 7 is a flow diagram of a method for an initial set up process for the device of FIGS. 3A-3D to determine and memorialize chest electrode placement locations on a user, in accordance with some embodiments of the present disclosure.

DETAILED DESCRIPTION

It is to be understood that the present disclosure is not limited in its application to the details of construction, experiments, exemplary data, and/or the arrangement of the components set forth in the following description. The embodiments of the present disclosure are capable of other embodiments or of being practiced or carried out in various ways. Also, it is to be understood that the terminology employed herein is for purpose of description and should not be regarded as limiting.

In the following detailed description of embodiments of the present disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

An electrocardiogram (ECG) provides a number of ECG waveforms that represent the electrical activity of a person's heart. An ECG monitoring device may comprise a set of electrodes for recording these ECG waveforms (also referred to herein as "taking an ECG") of the person's heart. The set of electrodes may be placed on the skin of the person in multiple locations and the electrical signal (ECG waveform) recorded between each electrode pair in the set of electrodes may be referred to as a lead. Varying numbers of leads can be used to take an ECG, and different numbers and combinations of electrodes can be used to form the various leads. Example numbers of leads used for taking ECGs are 1, 2, 6, and 12 leads.

The ECG waveforms may be analyzed (typically after standard filtering and "cleaning" of the signals) for various indicators that are useful in detecting cardiac events or status, such as cardiac arrhythmia detection and character- ization. Such indicators may include ECG waveform ampli- tude and morphology (e.g., QRS complex amplitude and morphology), R wave-ST segment and T wave amplitude analysis, and heart rate variability (HRV), for example.

Figure 1:
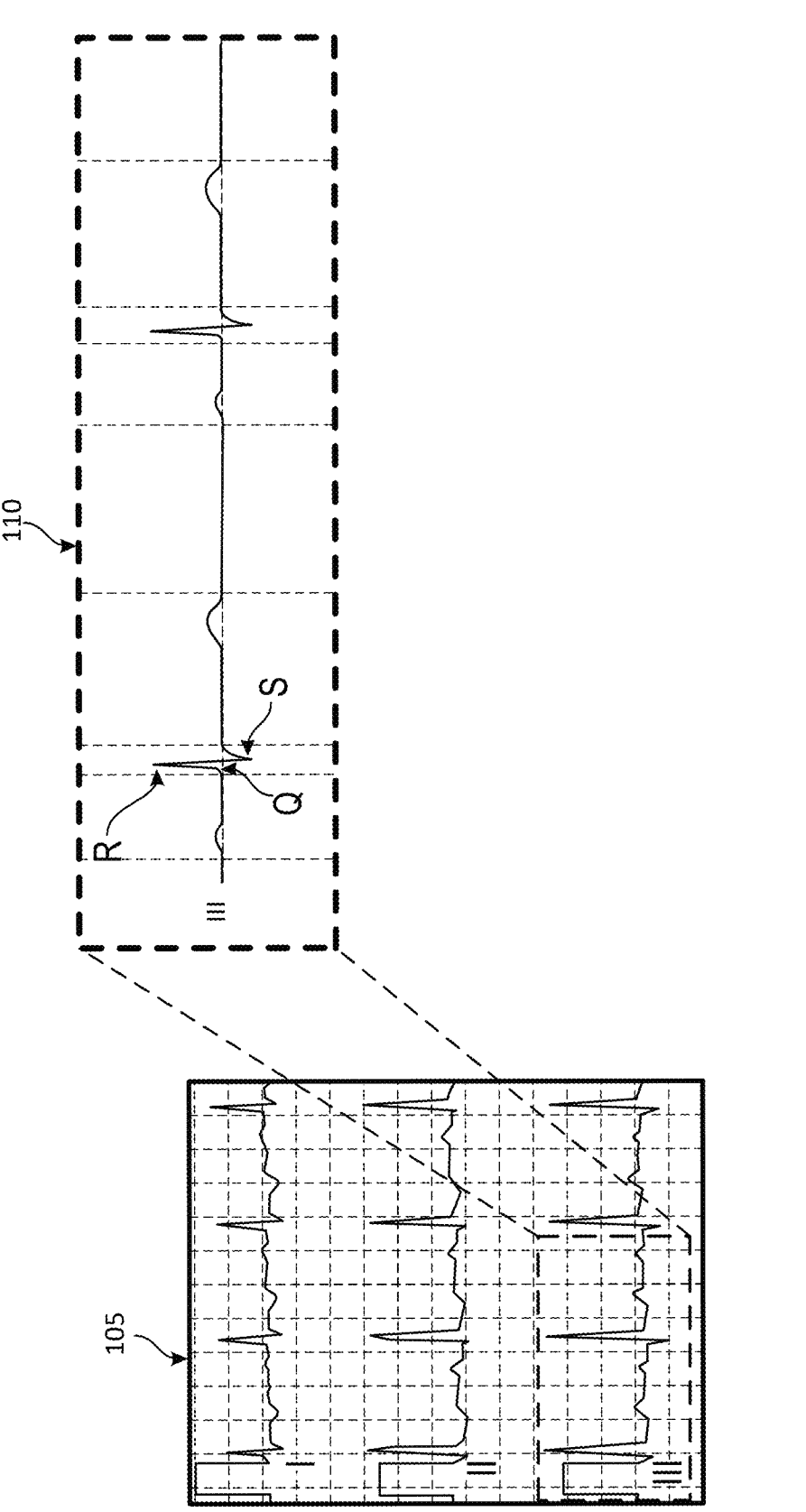
FIG. 1A is a diagram illustrating electrocardiogram (ECG) waveforms, in accordance with some embodiments of the present disclosure.

As noted above, ECG waveforms are generated from measuring multiple leads (each lead formed by a different electrode pair), and the ECG waveform obtained from each different electrode pair/lead may be different/unique (e.g., may have different morphologies/amplitudes). This is be- cause although the various leads may analyze the same electrical events, each one may do so from a different angle. FIG. 1 illustrates a view 105 of an ECG waveform detected by each of 3 leads (I, II, and III) when a 3-lead ECG is taken as well as an exploded view 110 of the ECG waveform measured by lead III illustrating the QRS complex. As shown, the amplitudes and morphologies of the ECG wave- form taken from leads I-III are all different.

There are different "standard" configurations for electrode placement that can be used to place electrodes on the person. For example, an electrode placed on the right arm can be referred to as RA. The electrode placed on the left arm can be referred to as LA. The RA and LA electrodes may be placed at the same location on the left and right arms, preferably near the wrist in some embodiments. The leg electrodes can be referred to as RL for the right leg and LL for the left leg. The RL and LL electrodes may be placed on the same location for the left and right legs, preferably near the ankle in some embodiments. Lead I is typically the voltage between the left arm (LA) and right arm (RA), e.g. I=LA−RA. Lead II is typically the voltage between the left leg (LL) and right arm (RA), e.g. II=LL−RA. Lead III is the typically voltage between the left leg (LL) and left arm (LA), e.g. III=LL−LA. Augmented limb leads can also be determined from RA, RL, LL, and LA. The augmented vector right (aVR) lead is equal to RA−(LA+LL)/2 or −(I+II)/2. The augmented vector left (aVL) lead is equal to LA−(RA+LL)/2 or I−II/2. The augmented vector foot (aVF) lead is equal to LL−(RA+LA)/2 or II−I/2.

Figure 2:
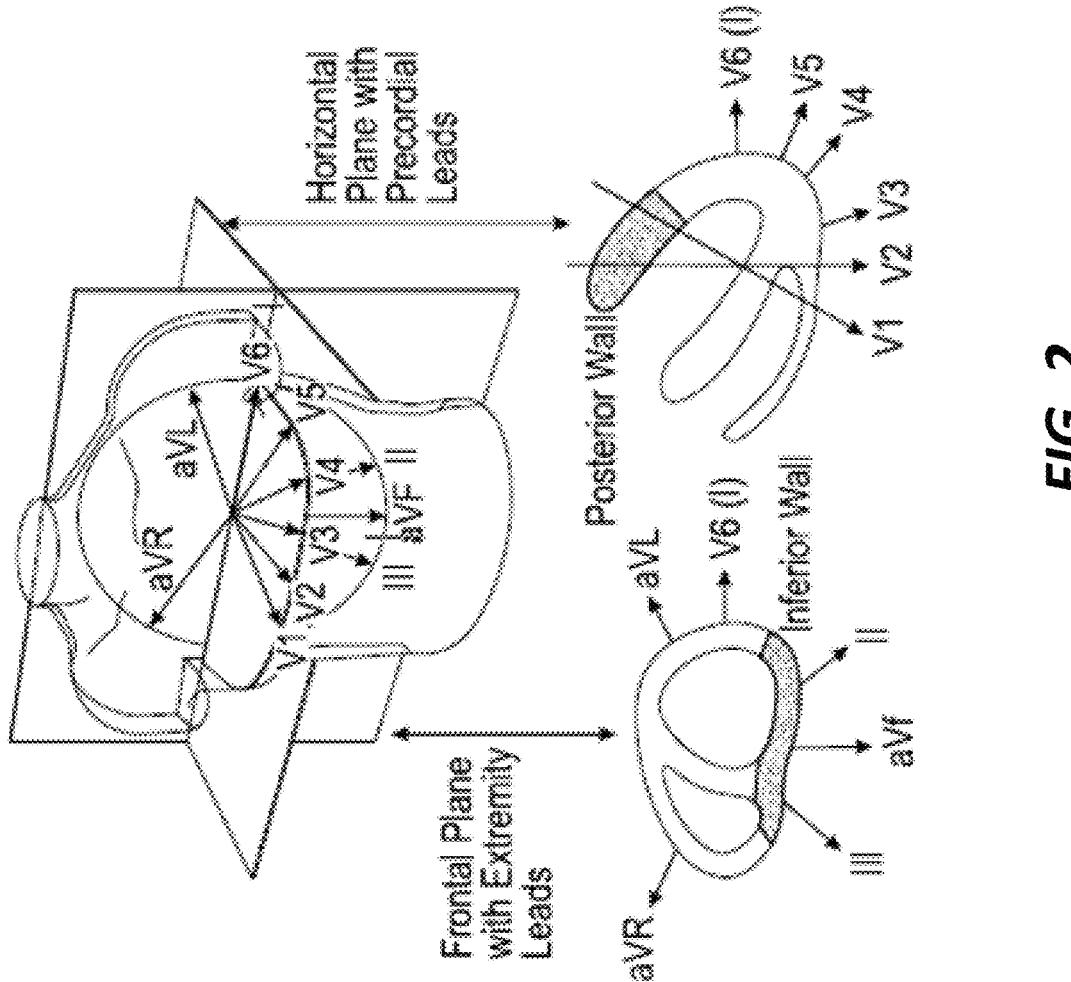
FIG. 2 illustrates a single dipole heart model with a 12 lead set represented on a hexaxial system, in accordance with some embodiments of the present disclosure.

FIG. 2 illustrates a single dipole heart model 115 with a 12 lead set comprising the I, II, III, aVR, aVL, aVF, V1, V2, V3, V4, V5, and V6 leads, all represented on a hexaxial system. The heart model 115 assumes a homogeneous cardiac field in all directions that only changes magnitude and direction with the cycle time. As illustrated in FIG. 2, there are 2 orthogonal planes, the frontal plane and the horizontal plane. Inside each plane, there are several leads to cover the whole plane. In the frontal plane, there are 2 independent leads I and II, and 4 other derived leads III, aVR, aVL, and aVF, each 30 degrees apart. The reason the frontal plane has 2 independent leads is that they are far-field leads, each of which can cover a wider perspective but provide less detail, like a wide-angle camera lens. In the horizontal plane, there are normally 6 independent leads which are all closer to the heart than limb leads and may be referred to as near-field leads. Following the same analogy of a camera, the near-field leads may behave like a zoom- lens that covers less perspective, but with more accuracy towards local activity like ischemia and infarction. The two orthogonal planes are related by using a synthetic reference point formed by Leads I & II, called the Wilson-Central- Terminal (WCT). It is defined as RA+LA+RL/3 but given that both Lead I and II are recorded with reference to the RA so that the voltage of the RA can be considered zero, the WCT (VW) can be calculated using the RA as the reference for both Leads I & II (thus, assuming it to have zero potential) as:

Lead I+Lead II/3.

Based on the above, when taking an ECG it is important to include one or more chest (horizontal plane) leads to provide an accurate ECG. In addition, as people age, their QRS and T-wave vector may gradually move from the frontal plane to the horizontal plane, thus increasing the importance of acquiring data from a horizontal plane lead. However, if a user wishes to perform an at home ECG that includes chest lead measurements, this requires the user to have knowledge of where on their chest they must place the electrodes of the portable ECG monitor that they are using. This is particularly difficult with chest leads as normally, determining the correct electrode placement location for chest leads requires a doctor or ECG technician to count the intercostal spaces across the patient's chest to find the proper placement for the chest leads (V1 through V6). This poses an issue when the patient wants to use a portable ECG measurement device for at-home monitoring, and needs to be able to place the electrodes in the proper locations themselves or receive assistance in doing so from a friend, caregiver, or family member who is not formally trained in the placement of ECG chest electrodes.

Embodiments of the present disclosure address the above and other problems by providing a device for determining and memorializing chest electrode placement locations on a user. The device utilizes two datum reference points in the patient's anatomy, the Jugular notch and the Xiphoid pro- cess, which are easily found and repeatable and which serve to ensure the device is in the correct position to memorialize chest electrode placement locations. The device may com- prise a first plate and a second plate operatively coupled to the first plate so that the second plate slides along a vertical axis of the first plate and the first plate slides along a vertical access of the second plate. The device may further comprise a template grid having a grid pattern defining a plurality of cells printed thereon. The template grid may have a coor- dinate system for identifying each of the plurality of cells.

The template grid may be modified to indicate a set of chest electrode placement locations on the user.

An initial set up process may be performed by a physician, care giver, or other trained professional, who may place the device on a chest of the patient and slide the first and second plates until a dimple of the first plate engages with a xiphoid process of a user and a dimple of the second plate slides engages with a jugular notch of the user. When the dimple of the first plate engages with the xiphoid process of the user and the dimple of the second plate engages with the jugular notch of the user, the device may be in the measurement position where the physician can memorialize determined placement locations of the chest electrodes on the template grid. The physician may lock the device in the measurement position using a set of holes on each of the first and second plate and any appropriate attachment mechanism to ensure that it is not inadvertently moved while determining and memorializing the chest electrode placement locations. The device may be provided to the user for use in determining chest electrode placement locations when performing at-home ECG measurements.

The device disclosed herein provides a means for a patient or caregiver to determine the appropriate location for chest electrode placement when performing an at-home ECG measurement, in an easy to use and quick manner. The patient's measurements can be easily read off the device and stored for future reference so that if the patient loses or damages their device, another device can be configured for them and sent to them without any re-measurement.

Figure 3A:
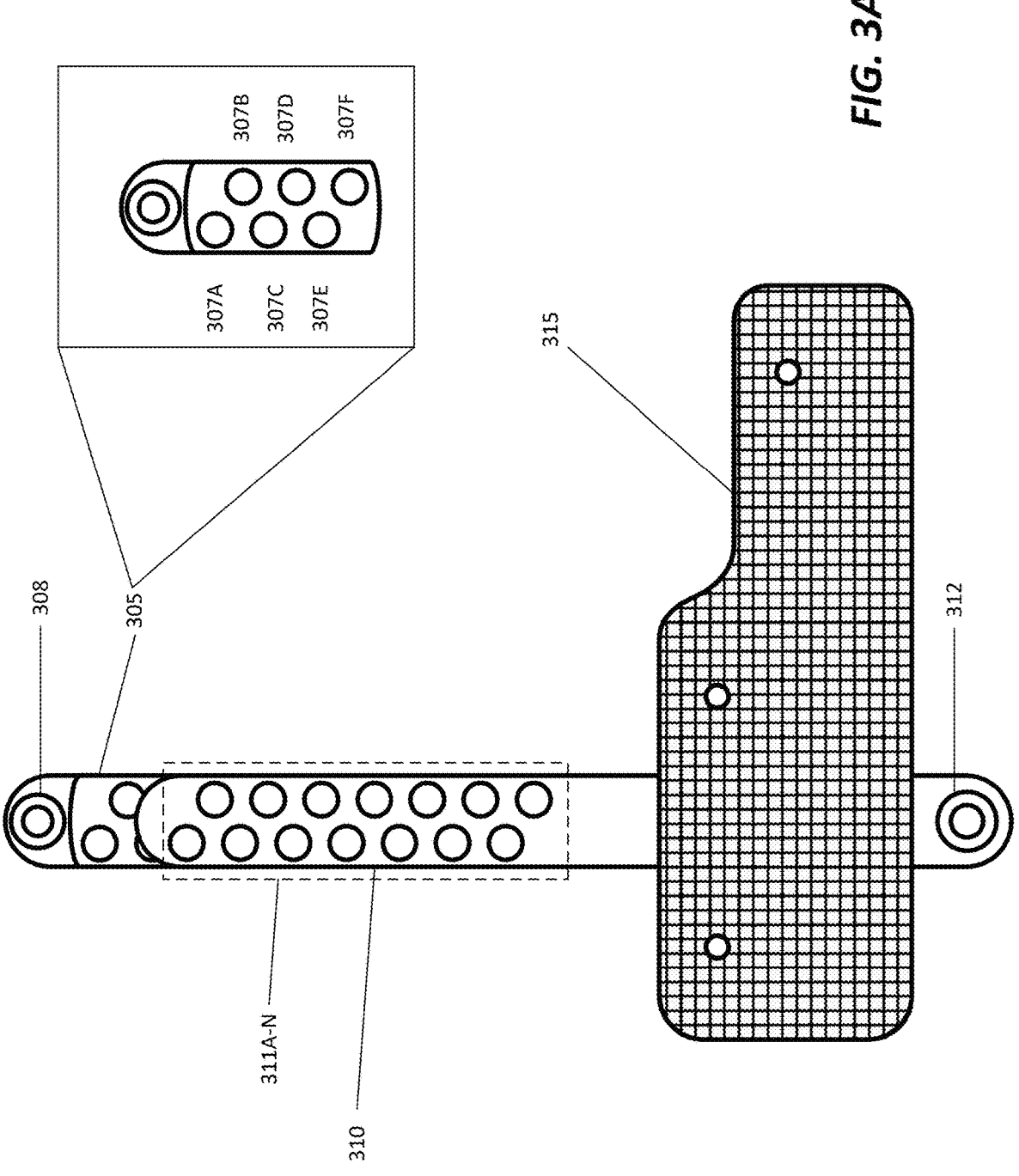
Figure 3B:
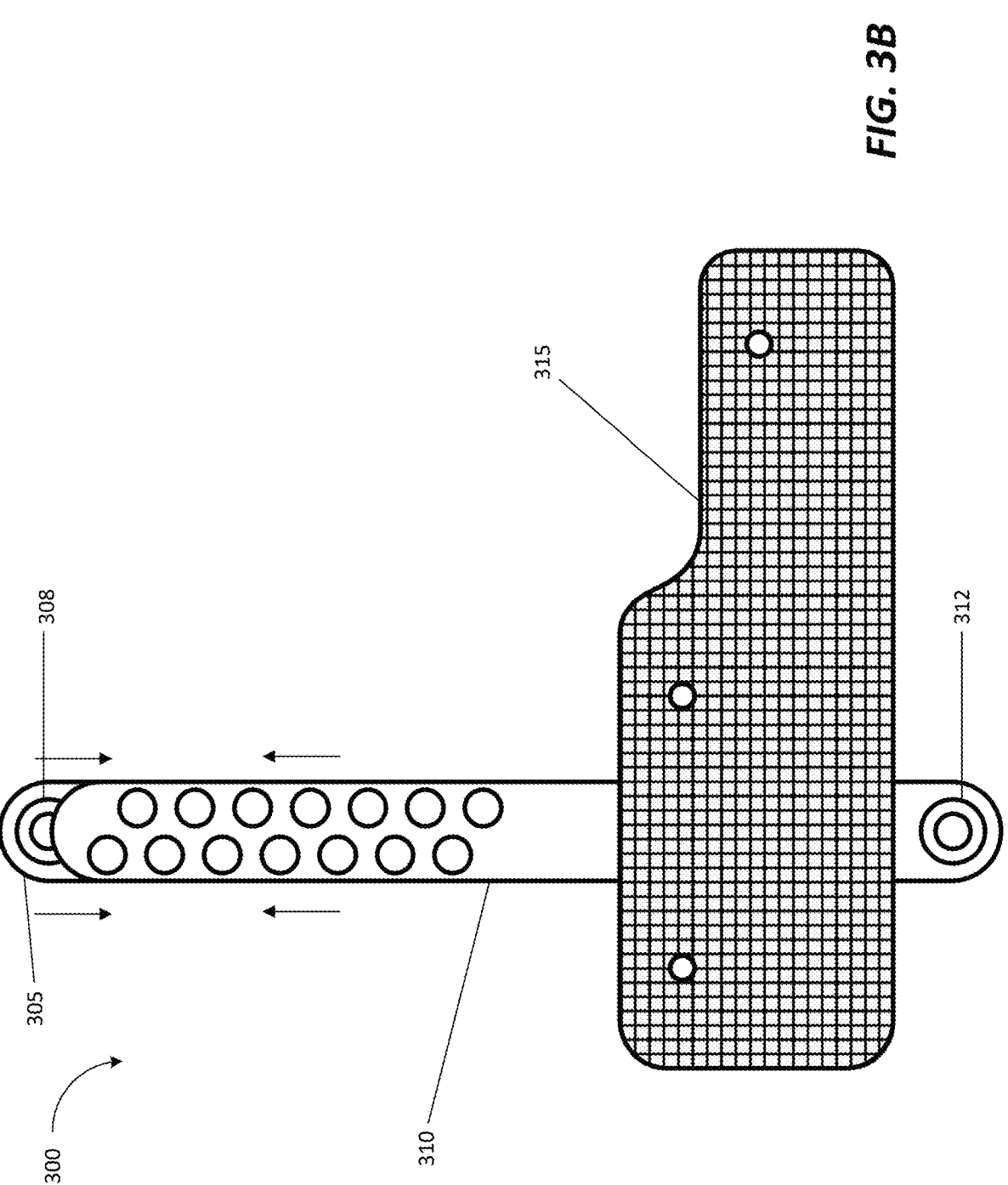

FIGS. 3A-3D illustrate a chest electrode template device 300 (hereinafter referred to as device 300) for determining and memorializing electrode placement locations on a user, as well as guiding the user in placing chest electrodes for performing an at-home ECG, in accordance with some embodiments of the present disclosure. The device 300 may include a jugular plate 305 and a xiphoid plate 310 having a template grid 315 mounted thereon. The jugular plate 305 and the xiphoid plate 310 may each comprise a die cut sheet of any appropriate biocompatible material such as ABS plastic, for example That has been die cut, molded, machined, or otherwise formed. The jugular plate 305 may be attached to the xiphoid plate 310 so that the jugular plate 305 may slide along the vertical axis of the xiphoid plate 310 and the xiphoid plate 310 may slide along the vertical axis of the jugular plate 305, as shown in FIG. 3B. The jugular plate 305 may be attached to the xiphoid plate 310 using any appropriate means. In one example, the side edges of the xiphoid plate 310 may define a track (not shown) in which the jugular plate 305 is inserted and may slide along the vertical axis of the xiphoid plate 310 while the xiphoid plate 310 may simultaneously slide along the vertical axis of the jugular plate 305.

Figure 9:
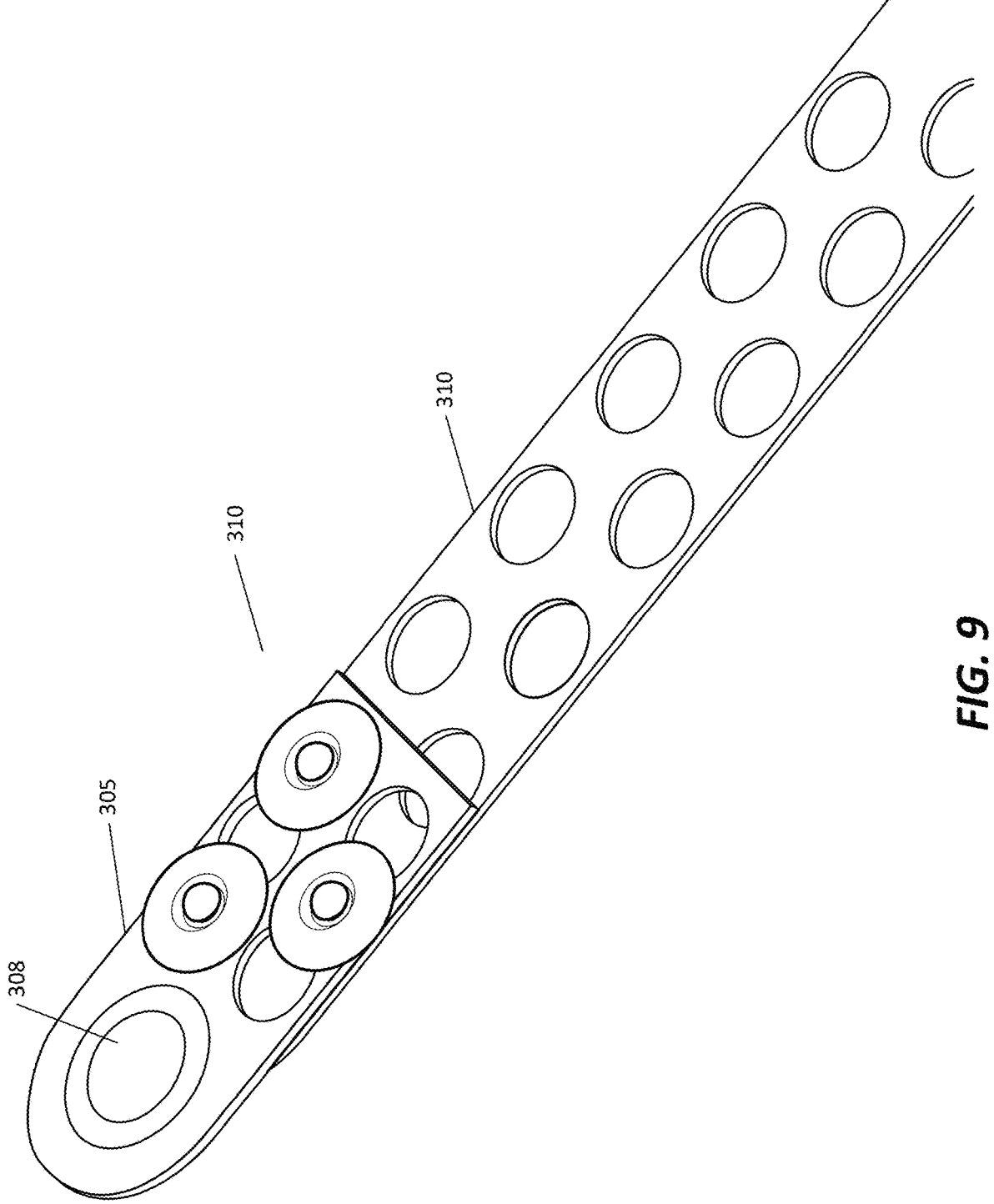
FIG. 9 illustrates the device of FIGS. 3A-3D when locked in the measurement position using the attachment mechanism of FIG. 8, in accordance with some embodiments of the present disclosure.

The jugular plate 305 may include a set of holes 307A-F and the xiphoid plate 310 may include a set of holes 311A-N as shown in FIGS. 3A-3C. Both sets of holes 307 and 311 may be sized to receive an attachment mechanism that will lock the jugular plate 305 in place on the xiphoid plate 310 as shown in FIG. 9.

Although the sets of holes 307 and 311 are illustrated as comprising circular holes for example purposes, this is not a limitation and the sets of holes 307 and 311 may comprise holes of any appropriate shape. In some embodiments, the shape of the holes in the sets of holes 307 and 311 may be based on a type of attachment mechanism used to lock the jugular plate 305 in place on the xiphoid plate 310, as described in further detail herein.

Figure 3D:
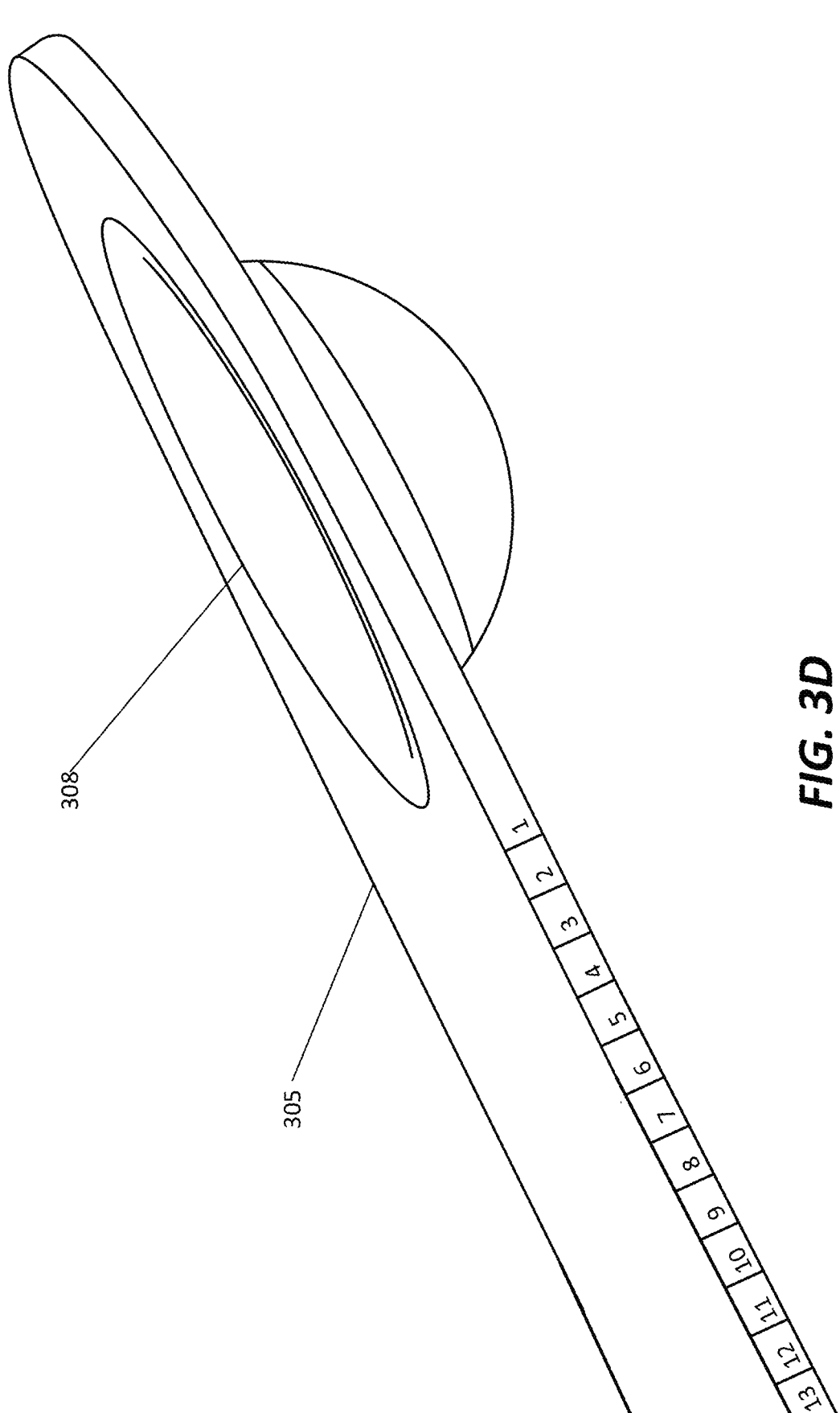
Figure 4A:
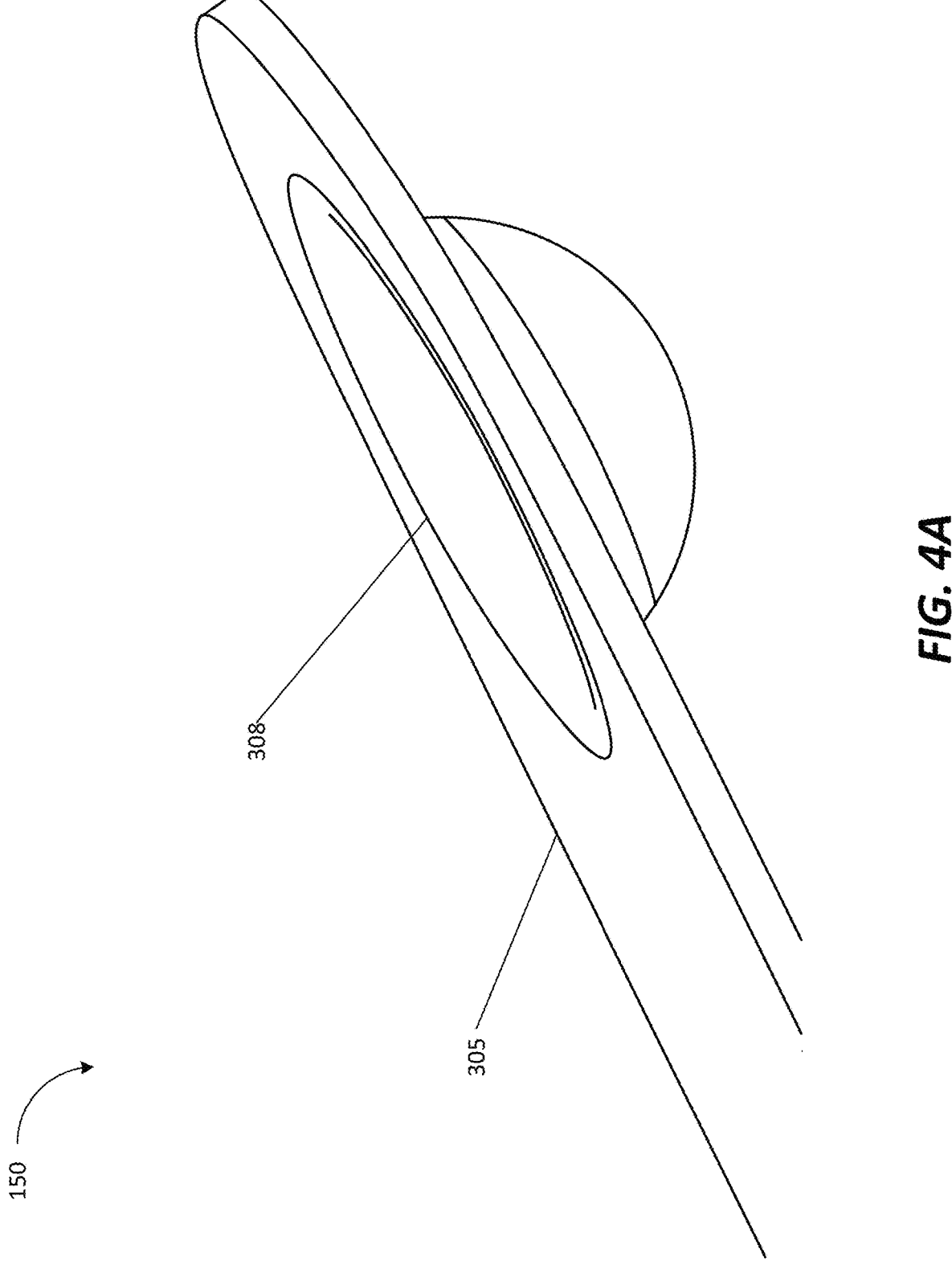
FIG. 4A illustrates a dimple of a first plate of the device of FIGS. 3A-3D, in accordance with some embodiments of the present disclosure.
Figure 6A:
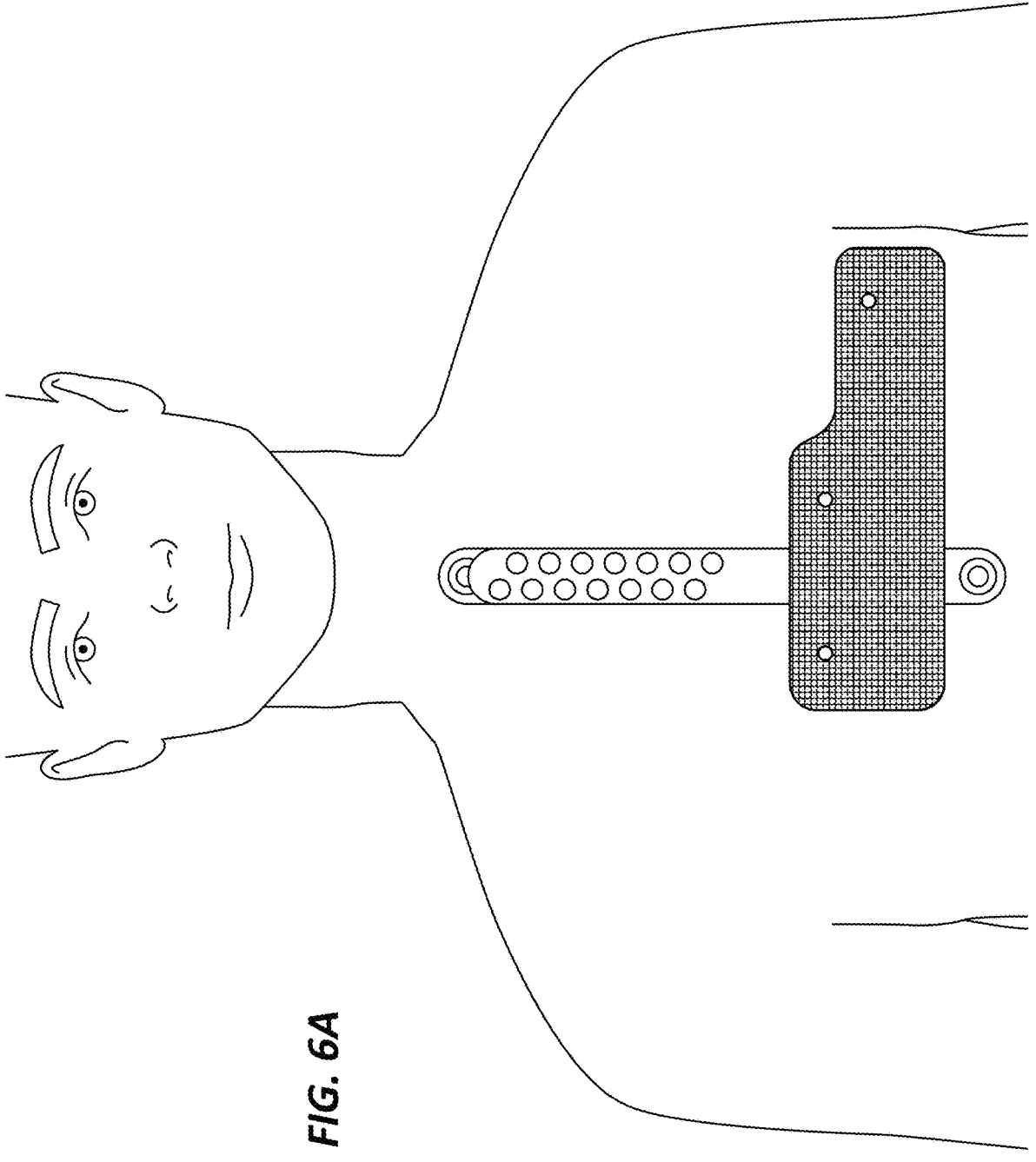
FIGS. 6A-6C illustrate the device of FIGS. 3A-3D during an initial set up process, in accordance with some embodiments of the present disclosure.

The jugular plate 305 may include a dimple 308 as shown in FIGS. 3C and 4A. The xiphoid plate 310 may include a similar dimple 312 shown in FIG. 3C. The dimple 308 may engage with (e.g., be pushed into) the patient's jugular notch, while the dimple 312 may engage with (e.g., be pushed into) the patient's xiphoid process (as shown in FIG. 6A), to serve as positioning datums for placing the template grid 315 on the patient as discussed in further detail herein. For example, a doctor may place the device 300 on the patient's chest as shown in FIG. 6A and slide the jugular plate 305 and the xiphoid plate 310 towards each other (or away from each other if necessary) until the dimple 308 engages with the patient's jugular notch and the dimple 312 engages with the patient's xiphoid process. When the dimple 308 engages with the patient's jugular notch and the dimple 312 engages with the patient's xiphoid process, the device 300 may be in what is referred to herein as the measurement position. The xiphoid process and jugular notch serve as immovable/immutable datum reference points for the sternum and surrounding anatomy (which includes the ribs, sternum and clavicles), under which the intercostal measurements, sternal borders and mid-clavicular lines referenced for placement of the chest ECG electrodes are taken. The dimple 308 may be formed on the jugular plate 305 and dimple 312 may be formed on the xiphoid plate 310 using any appropriate method such as thermoforming for example. The xiphoid plate 310 and jugular plate 305 may each include ruler-style distance markings anywhere on their body as shown in FIG. 3D to record the distance between the dimple 308 and the dimple 312 (i.e., the two positioning datums) once the device 300 is in the measurement position, as discussed in further detail herein. The ruler-style distance markings may utilize any appropriate unit of measurement, such as inches and centimeters for example. Although shown as on a first side of the jugular plate 305, this is not a limitation and the ruler-style markings may be located on either side, or on the top face of the jugular plate 305 (e.g., adjacent to the holes 307) or on a bottom face of the jugular plate 305. Similarly, the ruler-style markings may be located on either side, or on the top face of the xiphoid plate 310 (e.g., adjacent to the holes 311) or on a bottom face of the xiphoid plate 310.

Figure 8:
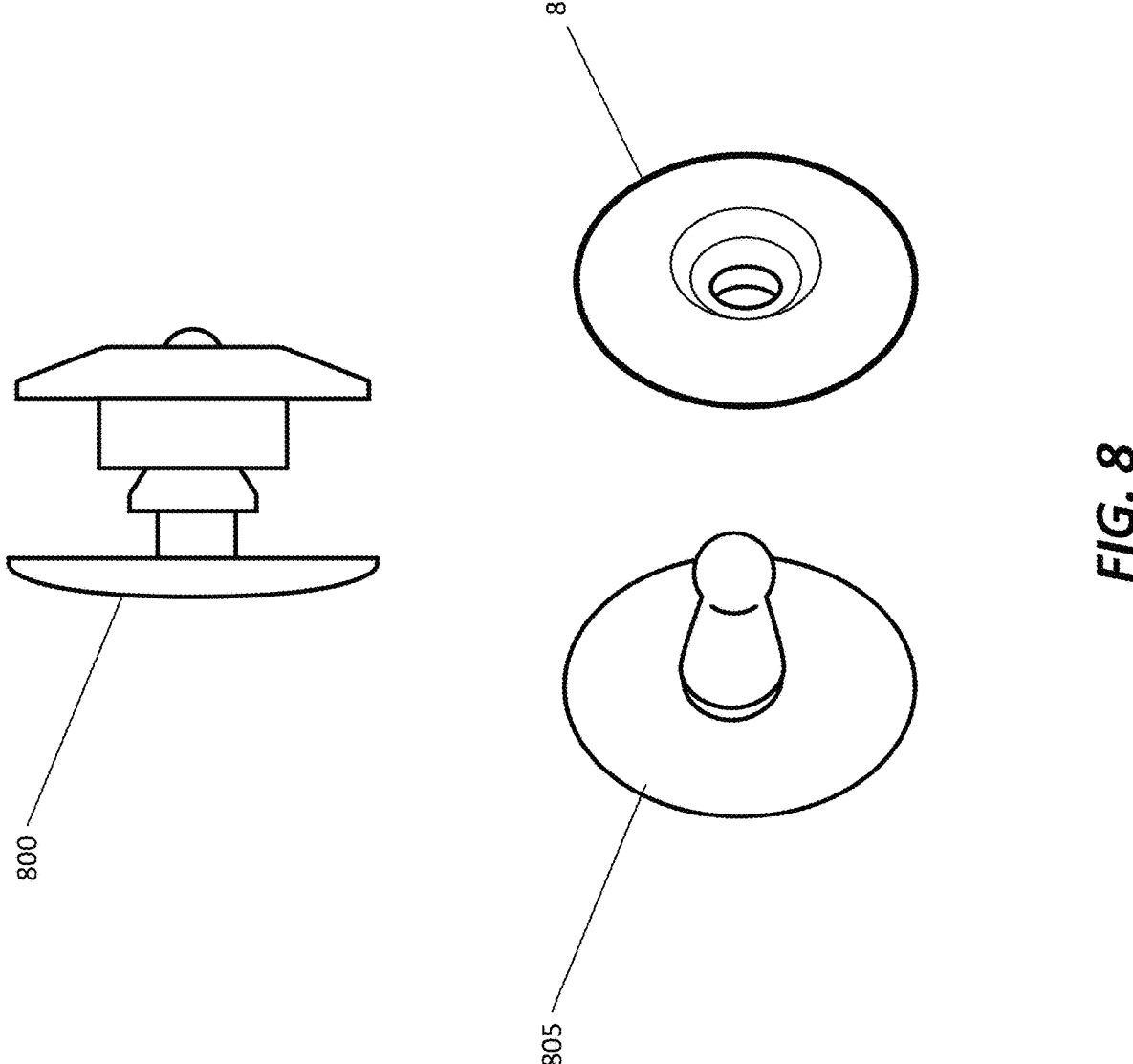
FIG. 8 illustrates an attachment mechanism, in accordance with some embodiments of the present disclosure.

When the device 300 is placed on a patient and reaches the measurement position, it may be locked in the measurement position using any appropriate attachment mechanism to lock the jugular plate 305 to the xiphoid plate 310 via the sets of holes 307 and 311. The attachment mechanism may be any appropriate attachment mechanism. In one example, the attachment mechanism may be a set of snap rivets similar to the snap rivet 800 as shown in FIG. 8. The snap rivet 800 may comprise a male component 805 and a female component 810. Under pressure, the male component 805 of the snap rivet 800 is pushed through the hole in the female component 810 to securely couple the male and female components together. After placing the device 300 in the measurement position and determining which holes from the set of holes 311 sufficiently overlap a corresponding hole from the set of holes 307 (as discussed in further detail herein), a snap rivet may be installed in each overlapping pair of holes as shown in FIG. 9 to secure the jugular plate 305 to the xiphoid plate 310.

The template grid 315 may comprise a thin sheet of biocompatible plastic, cloth, or other appropriate biocompatible material. In some embodiments, the template grid 315 may comprise any appropriate biocompatible material that is also sanitizable. The template grid 315 may have a grid pattern defining a plurality of cells printed on thereon so that electrode locations for any subset of or all of the V1, V2, V3, V4, V5, V6 chest leads can be recorded as discussed in further detail herein. For example, upon placing the device 300 on the patient, putting the device 300 into the measurement position and determining the electrode location for each required chest lead, the physician may mark each cell of the template grid 315 corresponding to a determined electrode location with a marker or similar writing utensil so that the device 300 can be removed from the patient before the template grid 315 is modified to permanently indicate each identified cell/electrode location. After marking each cell corresponding to an electrode location and removing the device 300 from the patient's chest, the physician may use any appropriate tool such as a hole punch, scissors, a punching tool, or a pen/pencil to cut out or punch out each cell corresponding to a chest electrode location. In some embodiments, the border of each cell of the template grid 315 may have pre-made perforations that make it easier to cut out or punch out. In this way, the template grid 315 may be modified to have permanent markings corresponding to the electrode location for each required chest lead.

Figure 4B:
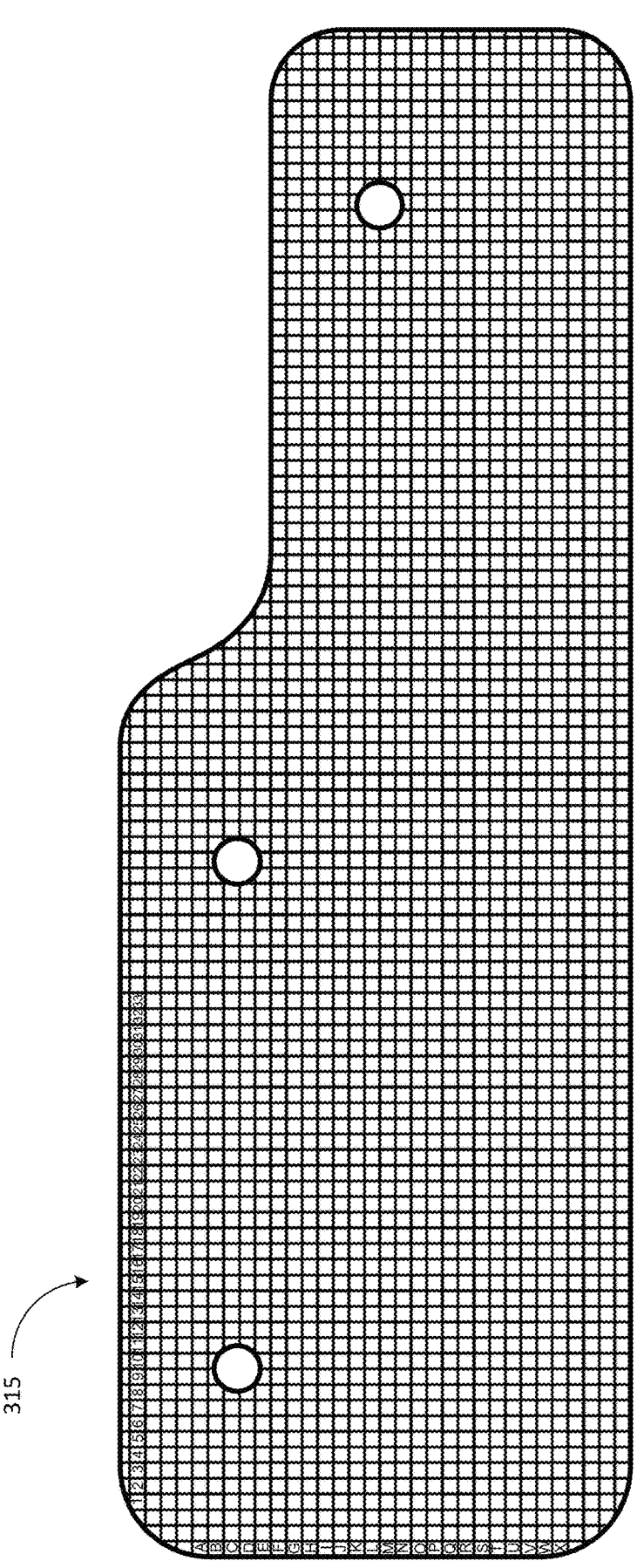
FIG. 4B illustrates a template grid of the device of FIGS. 3A-3D with a coordinate system printed thereon, in accordance with some embodiments of the present disclosure.

As shown in FIG. 4B, the template grid 315 may be labeled with a coordinate system including column and row markings that allows a doctor to record which cells of the template grid 315 correspond to the chest electrode locations. This information may be stored e.g., in a patient file of the patient for use in creating a new template if necessary, as discussed in further detail herein. The coordinate system may be printed on the template grid 315 in the same manner as the grid pattern. The template grid 315 may be attached to the xiphoid plate 310 using any appropriate method such as ultrasonic welding, heat-staking, use of glue or similar adhesives, or use of pressure sensitive adhesives, for example.

Figure 6B:
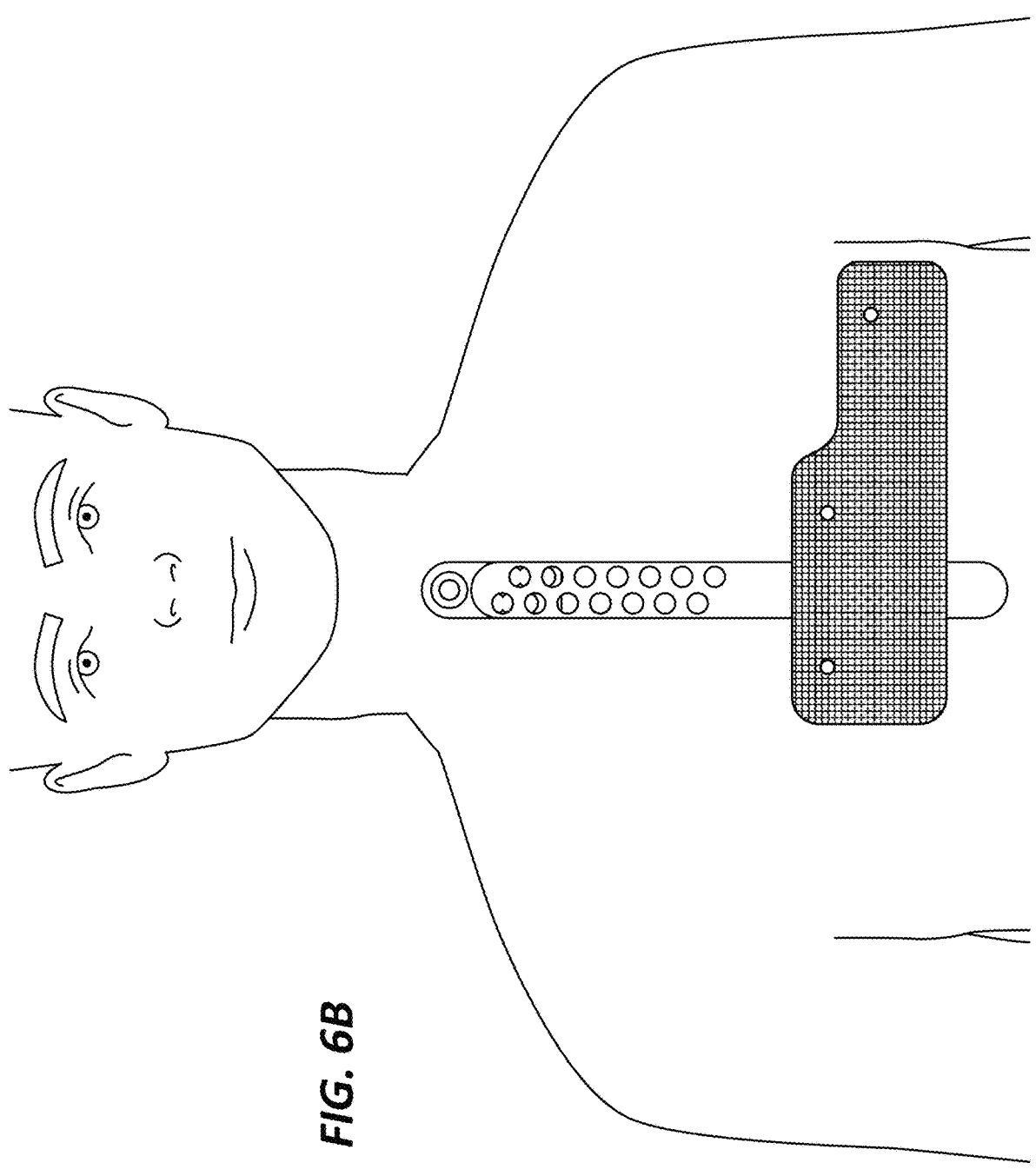
Figure 6C:

The size of the template grid 315 may be based on the electrode locations for each of the required chest leads. As can be seen in the example of FIG. 6C, the template grid 315 is sized to allow recording of the V1, V2, and V4 chest leads. However, if the required chest leads are V1, V2 and V3, the template grid 315 may be shorter horizontally. Although the template grid 315 is illustrated with the shape as shown in FIGS. 3A-3C and 6A-6C, this shape is not a limitation and the template grid 315 may be formed in any appropriate shape. In some embodiments, the shape of the template grid 315 is also based on the electrode locations for each required chest lead. For example (continuing to refer to FIG. 6C), if the V2, V3 and V4 chest leads are required, the template grid 315 may have a square shape to accommodate the electrode locations corresponding to those chest leads.

FIG. 7 is a method for an initial set up process for the chest electrode template device 300 described herein to determine and memorialize electrode placement locations on a user, in accordance with some embodiments of the present disclosure.

Figure 5:
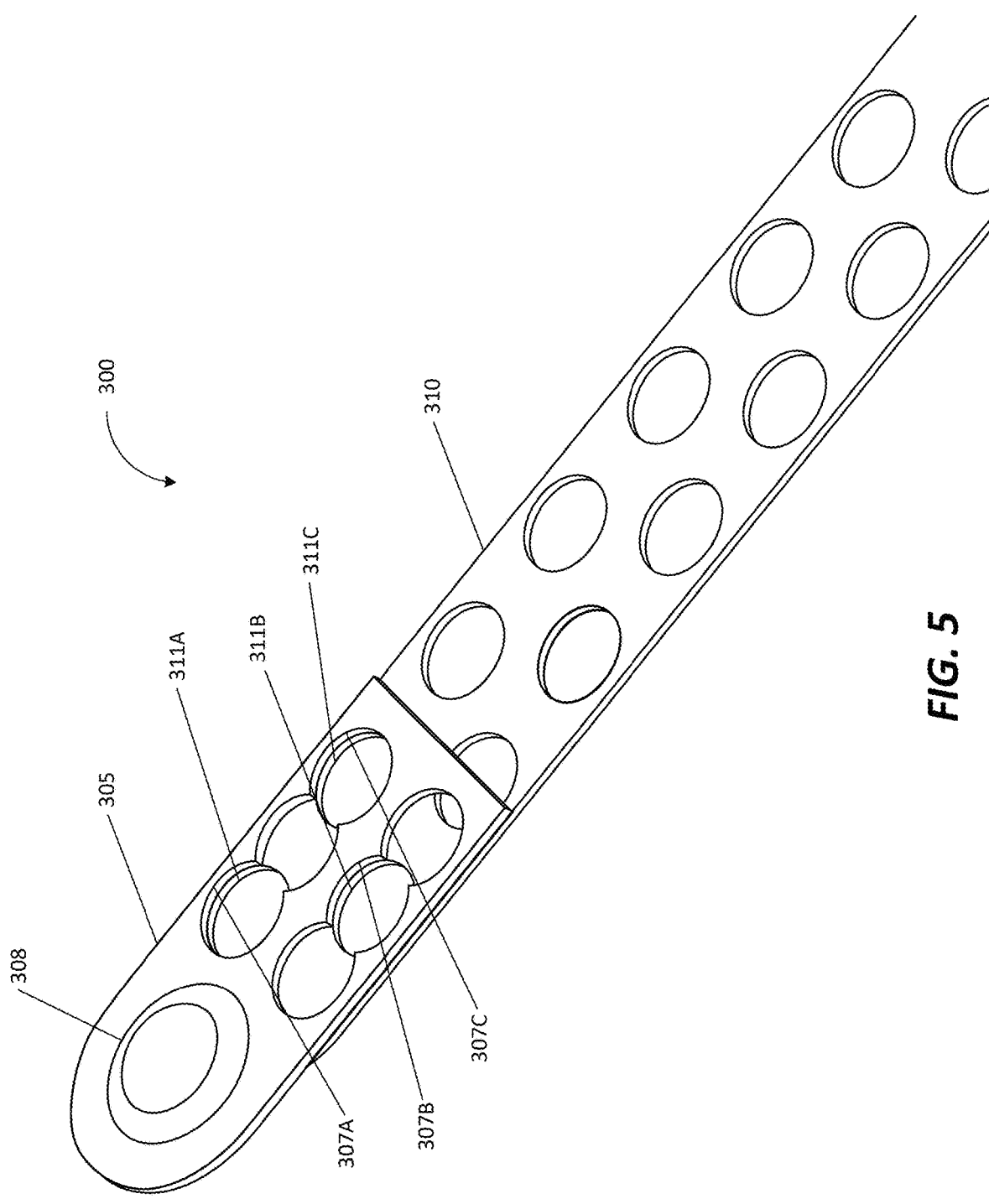
FIG. 5 illustrates the device of FIGS. 3A-3D in a measurement position, in accordance with some embodiments of the present disclosure.

Referring also to FIG. 6A, at block 705 a physician may place the device 100 on the patient's chest and slide the jugular plate 305 and the xiphoid plate 310 towards each other (or away from each other if necessary) until the dimple 308 engages with the patient's jugular notch and the dimple 312 engages with the patient's xiphoid process (i.e., until the device 300 is in the measurement position). It should be noted that there may be scenarios in which the physician may need to trim the shape of the template grid 315 with e.g., scissors, to more easily fit the anatomy of the patient. At block 710, once the device 300 is in the measurement position, the physician may determine a subset of the set of holes 311 on the xiphoid plate 310 that most closely overlap with (i.e., have the most overlap with) a corresponding hole 307 of the jugular plate 310. In some embodiments, the doctor may identify the three holes 311 on the xiphoid plate 310 that most closely overlap with a corresponding hole 307 of the jugular plate 305. It should be noted that identification of three holes is by example only and the physician may identify any appropriate number of holes 311 on the xiphoid plate 310 that most closely overlap with a corresponding hole 307 of the jugular plate 305 (e.g., two, four or five holes). In other embodiments, the physician may identify each hole 311 on the xiphoid plate 310 that has at least a threshold amount of overlap with a corresponding hole 307 of the jugular plate 305. In the example of FIG. 6B, the physician may determine that out of all the holes in the set of holes 311, holes 311A, 311B and 311C of the xiphoid plate 310 each have the most overlap with a corresponding hole 307 of the jugular plate 305 (i.e., holes 307A, 307B and 307C respectively) when the device 100 is in the measurement position. This is shown in FIG. 5 which illustrates an underside view of the device 300 when it is in the measurement position for the patient.

At block 715, the physician may then install a snap rivet into each of the 3 overlapping pairs of holes as shown in FIG. 9. This will lock the jugular plate 305 into its current position on the xiphoid plate 310. Snap rivets may be simple to press together but are not easy to take apart, so the patient and physician do not have to worry about them falling out and the physician does not have to worry about the patient making improper adjustments. Although described with respect to snap rivets, this is for example purposes only and any appropriate attachment mechanism may be used.

At block 720, the doctor may measure a length between the dimple 308 and the dimple 312 (the positioning datums) and record the length using the ruler-style markings on the jugular plate 305 and the xiphoid plate 310.

Referring also to FIG. 6C, at block 725, with the device 300 locked in the measurement position, the physician may determine the proper electrode locations for each of the required chest leads. More specifically, the physician may count the intercostal distances on the patient's chest to determine the proper electrode locations for each of the required chest leads (V1, V2 and V5 in the example of FIG. 6C) and may identify the coordinates of each cell of the template grid 315 that matches a determined electrode location. For example, the doctor may record the grid coordinates referenced by A, B, C (rows) and 1, 2, 3 (columns) that match each of the determined cells as shown in FIG. 6C to record the proper electrode locations for each required chest lead.

Upon recording the cell (based on e.g., the grid coordinates) corresponding to the electrode location for each required chest lead, at block 730 the physician may modify the template grid 315 to permanently indicate each identified cell. For example, the doctor may use any appropriate tool such as a hole punch, scissors, a punching tool, or a pen/pencil to cut out or punch out each identified cell. In some embodiments, the border of each cell may have pre-made perforations that make it easier to cut out or punch out. In this way, the template grid 315 includes permanent markings corresponding to the electrode locations for each of the required chest leads. The template grid 315 may allow the doctor to mark the identified cells with a marker or similar writing utensil so that the device 300 can be removed from the patient before the template grid 315 is modified to permanently indicate each identified cell. The physician may optionally, at block 735, trim the shape of the template grid 315 with e.g., scissors, to more easily fit the anatomy of the patient after modifying the template grid 315 to permanently indicate each identified cell.

Once the template grid 315 has been modified to permanently indicate each identified cell, the device 300 may be provided to the patient for future use in determining chest electrode placement locations. More specifically, the patient or caregiver may simply line up the template with the two datums on the patient's body by placing the device 300 on their chest such that the dimple 308 engages with the patient's jugular notch and the dimple 312 engages with the patient's xiphoid process. The patient or caregiver may then mark through the holes of the template grid 315 corresponding to the chest electrode placement locations with a washable marker or similar, and remove the template grid 315 and place the electrodes of the ECG monitoring device they are using on the marked locations on the patient's body.

As discussed herein, the distance between the dimple 308 and the dimple 312 and the chest electrode location coordinates (x,y) may be stored by the physician in an electronic profile associated with the patient. Thus, if the patient loses their chest electrode location template/device 300 or it is damaged, another can be reproduced without any re-measurement by the physician and can be sent directly to the patient.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Although the operations of the methods herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus comprising:
a first plate comprising:
  a first set of holes;
  a dimple configured to engage with a xiphoid process of a user when the first plate slides into a measurement position; and
  a template grid having a grid pattern defining a plurality of cells printed thereon, the template grid to indicate a set of chest electrode locations on the user; and
a second plate operatively coupled to the first plate so that the second plate slides along a vertical axis of the first plate and the first plate slides along a vertical access of the second plate, the second plate comprising:
  a second set of holes; and
  a second dimple configured to engage with a jugular notch of the user when the second plate slides into the measurement position.

2. The apparatus of claim 1, wherein each of the first set of holes and each of the second set of holes are sized to allow an attachment mechanism to be installed therein.

3. The apparatus of claim 1, wherein when the second plate slides into the measurement position, one or more of the first set of holes each overlap with a corresponding hole of the second set of holes.

4. The apparatus of claim 3, further comprising:
an attachment mechanism installed into each overlapping pair of holes to lock the second plate in the measurement position.

5. The apparatus of claim 4, wherein the attachment mechanism comprises a snap rivet.

6. The apparatus of claim 1, wherein the template grid further comprises a coordinate system printed thereon to indicate which cells of the plurality of cells correspond to a chest electrode location of the set of chest electrode locations on the user.

7. The apparatus of claim 6, wherein a border of each cell of the grid pattern comprises a perforation for removing the cell.

8. The apparatus of claim 1, wherein the template grid comprises a sheet of biocompatible plastic or a sheet of biocompatible cloth.

9. The apparatus of claim 1, wherein one or more of a size of the template grid and a shape of the template grid is based on the set of chest electrode locations.

10. The apparatus of claim 1, wherein the first and second plates each comprise a biocompatible material.

11. The apparatus of claim 1, wherein each of the first and second plates comprise:

distance markings to measure a distance between the first dimple and the second dimple when the second plate slides into the measurement position.

12. A method comprising:

placing on a chest of a user, a device comprising a first plate, a second plate and a template grid, wherein the second plate is operatively coupled to the first plate so that the second plate slides along a vertical axis of the first plate and the first plate slides along a vertical access of the second plate;

placing the device in a measurement position by sliding the second plate until a dimple of the second plate engages with a jugular notch of the user and sliding the first plate until a dimple of the first plate engages with a xiphoid process of the user;

locking the first plate and the second plate in the measurement position;

determining an electrode location for each of one or more chest leads; and modifying the template grid to indicate the determined electrode location for each of the one or more chest leads.

13. The method of claim 12, wherein locking the first plate and the second plate in the measurement position comprises:

determining a subset of the set of holes on the first plate that most closely overlap with a corresponding hole of the second plate when the device is in the measurement position; and using an attachment mechanism to secure the first plate to the second plate in the measurement position using the set of holes.

14. The method of claim 13, wherein the attachment mechanism comprises one or more snap rivets.

15. The method of claim 14, wherein using the attachment mechanism to secure the first plate to the second plate comprises:

installing each of the one or more snap rivets into a respective hole of the set of holes.

16. The method of claim 12, wherein the template grid comprises a grid pattern defining a plurality of cells, and wherein modifying the template grid to indicate the determined electrode location for each of the one or more chest leads comprises:

removing each cell that corresponds to a determined electrode location for the one or more chest leads.

17. The method of claim 16, wherein a border of each cell of the plurality of cells comprises a perforation to remove the cell.

18. The method of claim 16, wherein the template grid further comprises a coordinate system printed thereon to identify each cell of the plurality of cells.

19. The method of claim 18, wherein each of the first and second plates comprise distance markings, the method further comprising:

measuring a distance between a jugular notch of the user and a xiphoid process of the user when the device is in the measurement position using the distance markings of the first and second plates;

identifying each cell that corresponds to a determined electrode location for the one or more chest leads based on column and row markings corresponding to the cell; and storing the column and row markings corresponding to each cell that corresponds to a determined electrode location for the one or more chest leads and the measured distance between the jugular notch of the user and the xiphoid process of the user in a profile of the user.

* * * * *